United States Patent [19]

Rosenberg et al.

[11] 4,366,323
[45] Dec. 28, 1982

[54] POLYMERIZATION OF ARYLENE BIS-SILANOLS

[75] Inventors: Harold Rosenberg; Tsu-tzu Tsai, both of Dayton, Ohio

[73] Assignee: The United States of America as represented by the Secretary of the Air Force, Washington, D.C.

[21] Appl. No.: 343,000

[22] Filed: Jan. 27, 1982

[51] Int. Cl.$^3$ .............................................. C07F 7/08
[52] U.S. Cl. .................................. 556/433; 556/440; 556/457; 556/462; 528/21
[58] Field of Search ............... 556/462, 457, 440, 433

[56] References Cited

U.S. PATENT DOCUMENTS

| | | | |
|---|---|---|---|
| 2,562,000 | 7/1951 | Sveda | 556/433 X |
| 2,999,845 | 9/1961 | Goldberg | 260/17 |
| 3,117,149 | 1/1964 | Holdstock | 556/433 |
| 3,135,777 | 6/1964 | Nielsen | 556/433 |
| 3,202,634 | 8/1965 | Merker | 556/433 X |
| 3,539,655 | 11/1970 | Strachan et al. | 556/440 X |
| 3,595,974 | 7/1971 | Lloyd et al. | 260/448.2 B |
| 3,600,288 | 8/1971 | Viventi | 204/159.13 |
| 3,697,569 | 10/1972 | Mironov et al. | 260/448.2 B |
| 3,832,419 | 8/1974 | Merritt, Jr. | 260/824 R |

*Primary Examiner*—Paul F. Shaver
*Attorney, Agent, or Firm*—Donald J. Singer; Charles E. Bricker

[57] ABSTRACT

This invention is directed to the preparation of certain arylene bis-silanols in highly purified form and to the preparation of five new arylene bis-silanols in particular, along with a procedure for polymerizing these and other arylene-type bis-silanols using phosgene as a polymerization promotor or catalyst, to obtain highly purified, high molecular weight arylene-siloxanylene polymers having the characteristic structure:

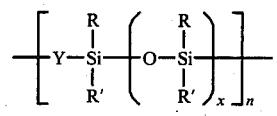

where Y is an arylene or substituted arylene moiety; R and R' are the same or different alkyl group(s), substituted alkyl group(s) or a phenyl group, x ranges from about 1 to 3 and n ranges from about 300 to 1500; said polymers having molecular weights (number average) of 100,000 and higher.

Preferred polymers are those arylenesiloxanylenecarbonate polymers which, when laminated to polycarbonate sheets or glass maintain their transparency, stability and adherence to said substrates at temperatures of up to and including 400° F. Such polymers are useful for the formulation of high temperature interlayers for windshields and canopies for aircraft and related aerospace vehicles.

4 Claims, No Drawings

POLYMERIZATION OF ARYLENE BIS-SILANOLS

RIGHTS OF THE GOVERNMENT

The invention described herein may be manufactured and used by or for the Government of the United States for all governmental purposes without payment of any royalty.

BACKGROUND OF THE INVENTION AND PRIOR ART

Prior to this invention, polysiloxanylenes containing recurring arylene backbone groups and, particularly, arylene backbone groups containing carbonate moieties, have not been successfully prepared in high molecular weights, viz., in molecular weights of 100,000 and above. Such arylenesiloxanylene polymers, prepared in accordance with prior art procedures, have demonstrated considerably lower molecular weights, and relatively poor physical and mechanical properties. These prior art polymers have no established practical application.

The polyarylenesiloxanylenes of the present invention are polymers having the characteristic structural formula:

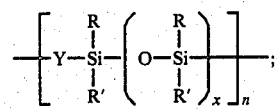

where Y is an arylene or substituted arylene moiety, preferably one which additionally contains a carbonate group; R and R' are the same or different alkyl group(s), substituted alkyl group(s) or a phenyl group, preferably lower alkyl or substituted lower alkyl groups containing from 1 to 3 carbon atoms; x ranges from about 1 to 3; and n ranges from 300 to 1500, said polymers having molecular weights (number average) of 100,000 and higher. This structural formula is referred to hereinafter as Formula A. The present invention permits the synthesis of highly pure arylene bis-silanol monomers and their polymerization in the presence of phosgene and an aromatic heterocyclic amine inert to reaction with phosgene, e.g., pyridine, methyl pyridine, cholidines and the like, to obtain high molecular weight homopolymers and copolymers, many of which are transparent, exhibit good adhesion to polycarbonates and glass and can withstand temperatures as high as 400° F. without degradation. Characteristically, the arylenesiloxanylene polymers, including those containing organocarbonate groups, prepared in accordance with this invention, exhibit viscosities beyond one deciliter per gram (1 dl/g). Additionally, these polymers display good mechanical properties for practical applications. The polymers of this invention provide base materials for high temperature-resistant, optically-transparent elastomers suitable for use in such applications as interlayer sheet materials for the fabrication of laminated sfaety glass-type aircraft windshields and canopy assemblies.

The present invention relates to the synthesis of highly purified bis-silanols, such as, bis[(4-hydroxydimethylsilyl)phenyl]carbonate, bis[4-(1-hydroxy-1,1,3,3-tetramethyldisiloxanyl)phenyl]carbonate, bis(3-hydroxydimethylsilylphenyl)carbonate, bis[3-(1-hydroxy-1,1,3,3-tetramethyldisiloxanyl)phenyl]carbonate, bis[4-(1-hydroxy-1,1,3,3-tetramethyldisloxanyl)]-benzene and their polymerization with phosgene (carbonyl chloride) to form high molecular weight siloxanylene polymers.

The highly pure bis-silanols obtained in accordance with this invention are essential in the synthesis of the desired high molecular weight siloxanylene polymers. It is well known that silanols, especially in the presence of a catalytic amount of acid or base, or at a high temperature, undergo condensation reactions to form siloxanes in accordance with the following equation:

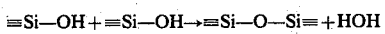

Thus, in the prior preparation of arylene bis-silanols, siloxanes were usually formed. This reaction not only consumed the synthesized silanols, but the siloxane formed an oily mixture with the silanol, which mixture, in many cases, could not be separated adequately. As a result of the aforementioned side reaction, many silanols which have been prepared by existing literature methods are virtually impure compounds and tend to form only low molecular weight polysiloxanes when polymerized.

In accordance with the present invention, however, pure bis(4-hydroxydimethylsilylphenyl)carbonate and bis[4-(1-hydroxy-1,1,3,3-tetramethyldisiloxanyl)-phenyl]carbonate, together with its corresponding meta analog, were prepared starting with 3- or 4-bromophenol.

Although certain of the reactions which were utilized to prepare select monomers in accordance with a new five (or seven)step synthesis for the production of high molecular weight, carbonate-containing, arylene siloxanylene polymers of this invention are based on reactions indicated in Lloyd, et al., U.S. Pat. No. 3,595,974 and Mironov, et al., U.S. Pat. No. 3,697,569; the procedures indicated in these Lloyd, et al., and Mironov, et al., patents were found inadequate for providing intermediates and monomers of the high purity required to obtain the high molecular weight polymers of this invention. For example, 4-dimethylsilylphenol, the preparation of which is identified herein below in the detailed description of the invention as Step 3, was reported by Mironov in U.S. Pat. No. 3,697,569 to melt at 35° to 37° C. However, 4-dimethylsilylphenol was isolated by the present inventors as a compound melting at 61° C.

Similarly, although Lloyd, et al., U.S. Pat. No. 3,595,974 disclosed the preparation of several silylphenyl carbonate intermediates, the procedures disclosed fail to result in obtaining any pure bis[(4-hydroxydimethylsilyl)phenyl]carbonate. This is in sharp contrast with the synthesis procedure of this invention which results at each stage in a product which could be isolated in a high state of purity.

The preparation of siloxane-containing polymers containing carbonate and polysiloxy blocks has been reported in U.S. Pat. No. 2,999,845, issued to Goldberg. This Goldberg patent is directed to the preparation of such block copolymers by reacting dihydric phenols with a carbonate ester, and dimethyldichlorosilane. Although the Goldberg patent utilizes a phosgenation step in pyridine in the course of preparing the referenced Goldberg polymers for the generation of the carbonate linkages, no such reaction occurs in the present invention. It will be apparent that the specific polymerization step of this invention, using the phosgene in the presence of an aromatic heterocyclic amine inert to reaction therewith, e.g., pyridine, for obtaining the highly purified polymers, is readily distinguishable from the Goldberg patent and the other prior art mentioned herein in that the phosgene does not react to form such linkages. The block copolymers formed in accordance with this Goldberg patent contain hydrolytically unstable phenoxysilyl bonds in the polymer backbone structure. No such bonds are present in the polymers of this invention. The Goldberg phosgenation process for polymerization uses phosgene to form carbonate linkages whereas in this invention phosgene is used to promote the formation of siloxane linkages (probably by dehydrating silanols or acting as a polymerization catalyst to promote formation of siloxane bonds).

U.S. Pat. No. 3,832,419 issued to Merritt, Jr., is directed to the preparation of organopolysiloxane-polycarbonate block copolymers from halogen chain-stopped organopolysiloxane, dihydric phenol and phosgene in a process which uses ammonia as an acid acceptor in the initial dihydric phenol/halogen chain-stopped organopolysiloxane reaction. This reaction is then followed by phosgenation to form the copolymers apparently in a manner similar to Goldberg U.S. Pat. No. 2,999,845. Nowhere does Merritt, Jr. teach preparation of polysiloxanylene arylene carbonates.

BRIEF SUMMARY OF THE INVENTION

This invention is directed to the preparation of arylene bis-silanols in highly purified form having the general formula

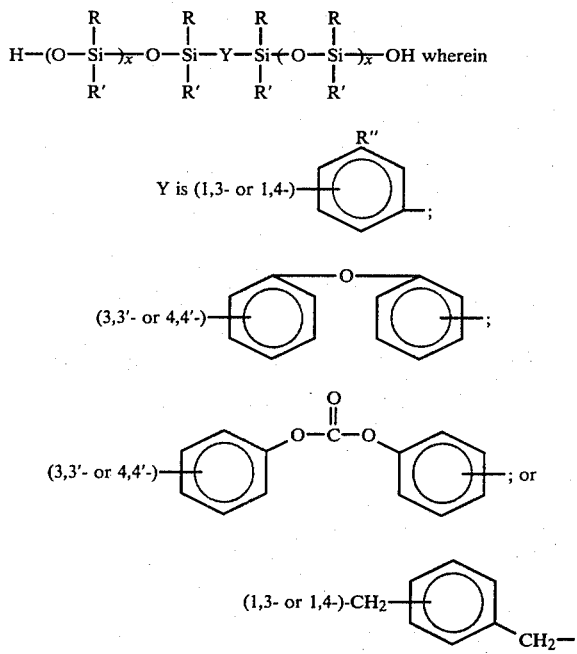

R and R' are the same or different alkyl group(s), substituted alkyl group(s) or a phenyl group, preferably lower alkyl groups or substituted lower alkyl containing from 1 to 3 carbon atoms, R'' is H, methyl or trifluoromethyl; and x is an integer having a value of 0 or 1 and polymerization of said bis-silanols in an aromatic heterocyclic amine inert to reaction with phosgene, e.g., pyridine solution, by the use of phosgene to obtain readily isolatable, high molecular weight polymers having the following structure:

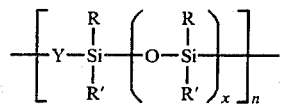

where x can range from 1 to 3, where n can range from about 300 to about 1500 and more usually ranges from about 500 to 850. Typical R and R' groups include methyl, ethyl, vinyl, propyl, isopropyl, phenyl and the like, including halogen-substituted R and R', such as, for example, 3,3,3-trifluoropropyl.

It is also possible, according to the process of this invention to produce copolymers by combining a co-monomer with the above-described arylene bis-silanol monomer and thereafter treat the blend of monomer and co-monomer with phosphene in the presence of the aforesaid aromatic heterocyclic amine. Such co-monomer has the same general formula as that given above, but differs from the monomer. Preferably, the co-monomer has a vinyl group in at least one of the R or R' positions. The ratio of monomer to co-monomer may be in the approximate range of 10:1 to 1:10.

It will be observed that in some of the polymers of this invention, the polymer's backbone structure will not contain the carbonate linkage even though phosgene is employed in the polymerization step. The phosgene herein acts essentially as a polymerization catalyst to promote formation of siloxane linkages (probably by dehydration of the bis-silanols).

These arylene bis-silanols are prepared by various procedures leading to the preparation of arylene bis-hydride precursors which are converted to the corresponding bis-hydroxy compounds by a catalytic oxidation-type reaction.

Novel carbonate-containing arylene bis-silanols are obtained by procedures involving a 5- (or 7-) step reaction sequence starting with bromophenols. The bromophenols are converted to siloxybromobenzene derivatives, which are then successively reacted to form phenoxysilyl hydrides, silylphenols, bis-silylphenylcarbonates, and finally bis-hydroxyphenylcarbonates.

The thus synthesized arylene bis-silanol monomers are then polymerized with phosgene, viz., carbonyl chloride, in the presence of the aforesaid type of aromatic heterocyclic amine to yield the desired high molecular weight polymers of this invention.

DETAILED DESCRIPTION OF THE INVENTION

According to the present invention, there are synthesized highly purified arylene bis-silanols, and especially carbonate-containing monomers, such as bis(4-hydroxydimethylsilylphenyl)carbonate; bis[4-(1-hydroxy-1,1,3,3-tetramethyldisiloxanyl)-phenyl]carbonate; bis(3-hydroxydimethylsilylphenyl)carbonate; bis[3-(1-hydroxy-1,1,3,3-tetramethyldisiloxanyl)phenyl]carbonate and bis[4-(1-hydroxy-1,1,3,3-tetramethyldisiloxanyl)]benzene, which are polymerized by use of phosgene to form high molecular weight arylenesiloxanylene polymers.

While the demonstrative 5-step synthesis and polymerization description herein below is given specifically in respect of the synthesis of bis[4-(1-hydroxy-1,1,3,3-tetramethyldisiloxanyl)phenyl]carbonate and its polymerization by the use of phosgene, it should be observed that any of the previously mentioned carbonate-containing arylene bis-silanols can likewise be synthesized and polymerized in accordance with such procedures.

STEP 1

Preparation of 4-bromophenoxydimethyldisilane

To a solution of 346.0 g (2.0 mol) of 4-bromophenol in 400 ml of toluene was added slowly 140.0 g (1.05 mol) of 1,1,3,3-tetramethyldisilazane. After the addition was complete, the reaction mixture was heated to reflux for 3 hours. After toluene was removed by evaporation under nitrogen, vacuum distillation at 2 mm/85°–95° C. gave 328.0 g (71%) of the expected compound, nmr; $\delta$, O(d, 6, SiC$\underline{H}$_3); 4.6 (septet, 1, Si$\underline{H}$); 6.6 (m, 4.2, $\phi\underline{H}$).

STEP 2

Preparation of 4-dimethylsilylphenoxydimethylsilane

To a three-necked 2-1 flask containing 37.0 g (1.52 mol) of magnesium, 94.0 g (1 mol) of dimethylchlorosilane and 100 ml of freshly-distilled tetrahydrofuran was added slowly and under nitrogen a solution of 328.0 g (1.42 mol) of 4-bromophenoxydimethylsilane and 94.0 g (1 mol) of dimethylchlorosilane. During the addition, the reaction temperature was kept at 40°–50° C. After the addition was complete, the reaction mixture was refluxed and part of the tetrahydrofuran was removed by distillation. After cooling, the inorganic salt was precipitated by petroleum ether (b.p. 30°–60° C.) and filtered. The filtrate was concentrated on a rotary evaporator and then vacuum distilled. The expected compound (234.0 g, 78.5%) distilled at 85°–95° C./3.5 mm.

Calcd. for C$_{10}$H$_{18}$O Si$_2$O:C,57.06; H, 8.62; Si, 26.71; mol wt 210.33.

Found: C, 57.10; H, 8.69; Si, 25.80; mol wt. 234.00 (VPO). nmr; $\delta$, O (m, 13, SiC$\underline{H}$_3) 4.17 (septet, 1, Si$\underline{H}$) 4.76 (septet, 1, Si$\underline{H}$); 6.6–7.17, (m, 4.3, $\phi\underline{H}$).

STEP 3

Preparation of 4-dimethylsilylphenol

To a cold solution ($\sim$9° C.) of 26.0 g of 4-dimethylsilylphenoxydimethylsilane in 250 ml of diethylether was added 10 ml of a solution of sodium methoxide (0.4 N) in methanol and the mixture stirred overnight. Solvents were removed by evaporation on a rotary evaporator at room temperature to yield 15.6 g (83.0%) of crude product, m.p. 59°–60° C. After recrystallization from hexane, the phenol was obtained as needles, m.p. 61° C.

Calcd for C$_8$H$_{12}$SiO: C, 63.09; H, 7.95; Si, 18.44; mol. wt. 152.27.

Found: C, 62.92; H, 8.01; Si, 18.52; mol. wt. 164 (VPO). nmr: $\delta$, o, (d, 6, SiC$\underline{H}$_3); 4.1 (m, 1.6, Si$\underline{H}$ and $\phi$O$\underline{H}$;) 6.3–7.17 (m, 4, $\phi\underline{H}$).

STEP 4

Preparation of bis(4-dimethylsilylphenyl)carbonate

To a cold ($\sim$ $-21$° C.) solution of 60.5 g. (0.40 mol.) of 4-dimethylsilylphenol, 100 ml of pyridine and 500 ml of toluene, was added slowly 28.0 g (0.28 mol.) of phosgene in 300 ml of toluene. After the addition was complete, the cooling bath was removed and the reaction mixture was stirred overnight. The pyridine salt formed was removed by filtration and the filtrate washed three times with aqueous sodium chloride solution. The organic layer was dried over anhydrous magnesium sulfate and concentrated on a rotary evaporator. Upon cooling of the residue, there was obtained 53.0 g (79.8%) of crude product. The carbonate was recrystallized from hexane to yield crystals, m.p. 72°–73° C.

Calcd. for C$_{17}$H$_{22}$Si$_2$O$_3$: C, 61.48; H, 7.15; Si, 16.91; mol. wt. 332.09.

Found: C, 61.27; H, 6.77; Si, 17.03; mol. wt. 334 (VPO). nmr: O (d, 6, SiC$\underline{H}$_3); 4.1 (septet, 0.9, Si$\underline{H}$); 7.03 (m, 4.1, $\phi\underline{H}$).

STEP 5

Preparation of bis(4-hydroxydimethylsilylphenyl)carbonate

To a cold ($\sim$0° C.) solution of 14.0 g of bis(4-dimethylsilylphenyl)carbonate in 200 ml. of distilled tetrahydrofuran and 25 ml of water was added slowly 15.0 g of silver acetate accompanied by vigorous stirring. After the addition was complete, the solution was stirred at 0° C. overnight. The solid formed was removed by filtration and the filtrate washed with saturated sodium chloride solution until no acid was detected. The organic layer, dried over anhydrous magnesium sulfate and concentrated on a rotary evaporator to a thick liquid, solidified upon standing. There was obtained 13.0 g (84.6%) of the expected product, m.p. 93°–4° C. The pure compound was obtained by recrystallization from benzene and hexane solution, m.p. 106° C.

Calcd. for C$_{17}$H$_{22}$Si$_2$O$_5$: C, 56.32; H, 6.12; Si 15.50; mol. wt. 362.53.

Found: C, 56.89; H, 6.31; Si 15.00; mol. wt. 361 (VPO), nmr: $\delta$, O (s, 11.4, SiC$\underline{H}$_3); 1.3 (s, 2, O$\underline{H}$); 6.8–7.3 (m, 8.3 $\phi\underline{H}$).

Where it is desired to prepare very specialized carbonate-containing arylene bis-silanols, viz., disiloxanyl-type phenyl carbonate monomers, the below indicated STEPS 6 and 7 are conducted. In other words, STEPS 6 and 7 are extensions of the basic 5-step procedure.

STEP 6

Preparation of bis[4-(1,1,3,3-tetramethyldisiloxanyl)phenyl]carbonate

To a cold (0° C.) solution of 15.0 g (0.04 mol) of bis(4-hydroxydimethylsilyl)phenylcarbonate in 75 ml. of toluene and 45 ml. of triethylamine was added 12.0 g (0.13 mol) of dimethylchlorosilane. After the addition was complete, the mixture was stirred overnight. The solid was removed by filtration and the filtrate washed with water, dried over anhydrous magnesium sulfate and concentrated on a rotary evaporator. Vacuum distillation of the residue at 170°¼° C./0.10 mm gave 16.5 g (84%) of the product.

Calcd. for C$_{21}$H$_{34}$Si$_4$O$_5$: C, 52.68; H, 7.16, Si, 23.46; mol. wt. 478.80.

Found: C, 52.87; H, 7.27, Si, 23.46; mol wt. 470 (VPO). nmr: $\delta$, 0–0.2 (d, s, 24, HSiC$\underline{H}$_3), $\phi$SiC$\underline{H}$_3) 5.16–4.66 (m, 2, Si$\underline{H}$); 7.9–7.2 (m, 8.2, $\phi\underline{H}$).

STEP 7

Preparation of bis[4-(1-hydroxy-1,1,3,3-tetramethyldisiloxanyl)-phenyl]carbonate To a cold ($-5$° C.) solution of 100 ml of acetone, 4 ml. of water and a catalytic amount of 5% palladium-on-carbon was added slowly 9.0 g of bis[4-(1,1,3,3-tetramethyldisiloxanyl)phenyl]carbonate in 20 ml. of acetone over a period of 8 hrs. After the addition was complete, the palladium-on-carbon was removed by filtration. The filtrate was concentrated on a rotary evaporator at room temperature to a viscous liquid which solidified upon treatment with pentane. There was obtained 7.5 g (78%) of the required compound. The carbonate was recrystallized from benzene and hexane solution to yield the pure compound, m.p. 62°–63° C.

Calcd for $C_{21}H_{34}Si_4O_7$: C, 49.38; H, 6.71; Si, 21.99; mol. wt. 510.80.

Found: C, 49.44; H, 6.81, Si, 22.11; mol. wt. 502 (VPO). nmr: δ, 0 (s, 12, $SiCH_3$); 0.24 (s, 12, $SiCH_3$); 1.8 (b, 2, $OH$); 7.3 (m, 10, $\phi H$).

STEP 8

Polymerization of bis[4-(1-hydroxy-1,1,3,3-tetramethyldisiloxanyl)-phenyl]carbonate Bis[4-(1-hydroxy-1,1,3,3-tetramethyldisiloxanyl)-phenyl]carbonate (3.0 g) and 10 ml. of freshly-distilled pyridine were placed in 50-ml. round bottomed flask, equipped with a magnetic stirring bar, a gas inlet tube which extended just above the reaction mixture, and a gas outlet leading into a sodium hydroxide solution. With the mixture stirred vigorously and cooled by an ice-water bath, phosgene was introduced slowly into the flask. A solid was formed in a few minutes and the solution became viscous and caked. Excess phosgene was then removed by sweeping the system with nitrogen. The reaction mixture was diluted with dichloromethane and stirred until the solid formed was loosened. The solution was concentrated to a small volume on a rotary evaporator before precipitating the polymer from methanol.

The equations shown herein below are included to illustrate the reactions which occur in each of the above enumerated STEPS 1 to 8, inclusive, described herein above. The number to the right of the equation corresponds to the step previously described which is involved in the synthesis and polymerization of the included compounds.

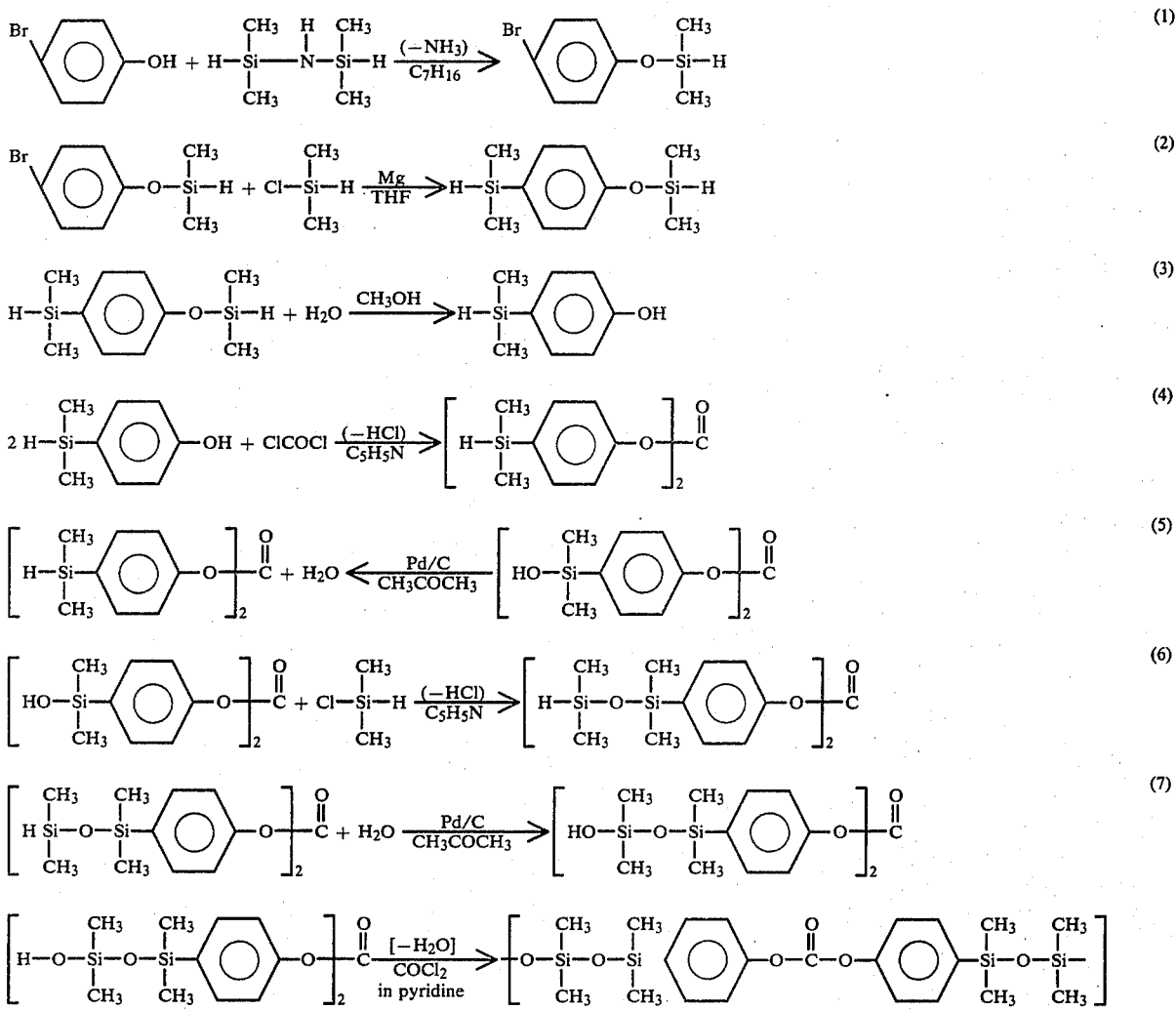

PROCESS OBSERVATIONS

The Grignard reaction shown in equation 2 above was conducted in situ with excess dimethylchlorosilane and magnesium in tetrahydrofuran solvent. The conventional method for conducting such Grignard reactions involves initial formation of the Grignard reagent, followed by a coupling reaction with dimethylchlrosilane. However, such conventional method was found to be inadequate for complete conversion of bromophenoxydimethylsilane to the dimethylsilylphenoxydimethylsilane. The bromophenoxydimethylsilane, if present in the product when the conventional method was involved, could not be removed by distillation. Hydrolysis of dimethylsilylphenoxydimethylsilane was carried out by introducing water into the mixture of the silane and methanol. It has been discovered that this particular order of addition must be followed or otherwise an undesirable rearrangement to the siloxybenzene (as shown by the following equation) will occur and there will be obtained an impure dimethylsilylphenol.

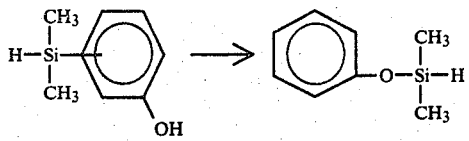

Pyridine was found to be the preferred acid-receptor reagent for phosgenation of the phenol in the reaction shown in Equation 4. Although triethylamine has been used in many similar reactions, it reacts with phosgene even at low temperatures. The product formed was found to be difficult to remove, especially from bis[(3-dimethylsilyl)phenyl]carbonate.

Pure bis-silanols could not be isolated readily if any impurities were present. The oxidation of the silicon-hydrogen bond of the silyl hydride to a silicon-hydroxy bond could be achieved either by the use of silver acetate or mercuric acetate in wet tetrahydrofuran or acetone solution or by utilization of the method of G. H. Barnes, Jr., et al., is published in the *Journal of Organic Chemistry* 31, 885 (1966). The Barnes et al, method involves use of palladium-on-carbon catalyst in wet polar solvents.

In certain of the procedures described in accordance with this invention, water and acetone were employed as the solvent system. The use of this solvent pair requires careful control over the reaction conditions as described herein above. They should be closely followed and precisely controlled in order to obtain the desired products in a highly pure condition.

Siloxane-containing bis-silanols can be prepared in the above indicated stepwise manner by initial synthesis of the siloxane-containing hydrosilanes as illustrated in Equation 6 above, followed by their oxidation to bis-silanols, as indicated in Equation 7 above.

Polymerization of carbonate-containing silanols has heretofore been extremely difficult to conduct, and in most cases cannot be effected, by conventional hetero-condensation of bis-silanols with diaminosilanes or by homocondensation reactions propagated by alkali reagents. Under these reaction conditions, the carbonate linkages readily decompose and form an undesired mixture of products. This degradation does not occur in accordance with the synthesis and polymerization procedures of this invention which permit the synthesis of carbonate-containing siloxanes of high molecular weight by treating bis-silanols with phosgene in pyridine solution at low ambient temperatures.

Although the mechanism of the polymerization reaction with respect to the role of phosgene has not been fully elucidated, it appears that the speed of the reaction is dependent on the reactivities of the respective silanols. It has been noted that bis-silanols with hydroxysilyl groups attached directly to the phenylene groups, such as bis[4(or 3-hydroxydimethylsilyl)phenyl]carbonate, reacted rapidly in the presence of phosgene and the polymerization was complete within several minutes. On the other hand, for bis[4(or 3)-(1-hydroxy-1,1,3,3-tetramethyldisiloxanyl)phenyl]carbonate, the reaction was much slower and it was necessary to react this monomer in the presence of phosgene until the solution became viscous and caked. The polymers obtained herein were all analyzed and characterized by conventional polymer analysis and characterization procedures.

Five new bis-silanol monomers have been synthesized in highly purified form and polymerized by use of phosgene and pyridine in accordance with this invention. They are: (1) bis(4-hydroxydimethylsilylphenyl)carbonate; (2) bis[4-(1-hydroxy-1,1,3,3-tetramethyldisiloxanyl)phenyl]carbonate; (3) bis(3-hydroxydimethylsilylphenyl)carbonate; (4) bis[3-(1-hydroxy-1,1,3,3-tetramethyldisiloxanyl)phenyl]carbonate and (5) bis[4-(1-hydroxy-1,1,3,3-tetramethyldisiloxanyl)]benzene. As will be apparent to those skilled in the art, monomers (1) through (4) already contain the carbonate linkage and, upon polymerization in accordance with this invention, will result in polymers retaining the carbonate linkage in the polymer backbone. Monomer (5), however, does not contain a carbonate linkage and its polymers do not contain the carbonate linkage upon homopolymerization.

This invention will be illustrated in additional detail in the examples which follow. In these examples, all parts, percents and ratios are by weight unless otherwise indicated.

EXAMPLE 1

Preparation of Bis(4-hydroxydimethylsilylphenyl)carbonate

This monomer was prepared in accordance with the detailed procedures set forth above in STEPS 1 through 5 to yield 13.0 g. (84.6%) of the expected product, m.p. 93°–4° C. The pure compound was obtained by recrystallization from benzene and hexane solution, m.p. 106° C.

Calcd for $C_{17}H_{22}Si_2O_5$: C, 56.32; H, 6.12; Si 15.50; mol wt. 362.53.

Found: C, 56.89; H, 6.31; Si 15.00; mol. wt. 361 (VPO) nmr: $\delta$, 0 (s, 11.4, SiC$\underline{H}_3$); 1.3 (s, 2, O$\underline{H}$); 6.8–7.3 (m, 8.2, $\delta\underline{H}$).

This monomer is useful in forming high molecular weight polysiloxanylenearylenecarbonate polymers which can be used as high temperature resistant interlayers when cured and laminated to glass or polycarbonate sheets according to laminating procedures well known in the art.

EXAMPLE 2

Preparation of Bis(3-hydroxydimethylsilylphenyl)carbonate

This new monomer was prepared from the starting material 3-dimethylsilylphenoxydimethylsilane (obtained in accordance with the synthesis procedure of STEPS 1 and 2 above except for using 3-bromophenoxydimethyldisilane in place of the corresponding 4-bromo compound of STEP 1).

To a solution of 122.1 g of 3-dimethylsilylphenoxydimethylsilane and 250 ml. of methanol was added 35.5 ml of distilled water. After the mixture was stirred overnight, the methanol was removed by evaporation at room temperature on a rotary evaporator. The concentrated solution was treated with toluene, dried over anhydrous magnesium sulfate and again evaporated on a rotary evaporator to yield 89.85 g. of the desired 3-dimethylsilylphenol.

To a cold (∼ −20° C.) solution of 60.5 g (0.40 mol.) of 3-dimethylsilylphenol, 100 ml of pyridine and 500 ml of toluene was added slowly 28.0 g. (0.28 mol.) of phosgene in 300 ml. of toluene. After the addition was complete, the cooling bath was removed and the reaction mixture was stirred overnight. The pyridine salt formed was removed by filtration and the filtrate washed three times with aqueous sodium chloride solution, dried over anhydrous magnesium sulfate and evaporated on a rotary evaporator. The desired material bis(3-dimethylsilylphenyl)carbonate was obtained by vacuum distillation as a liquid having a boiling point of 143° C./0.12 mm.

Calcd. for $C_{17}H_{22}Si_2O_3$: C, 61.48; H, 7.15; Si, 16.91; mol. wt. 332.09.

Found: C, 61.27; H, 6.77; Si, 17.03; mol. wt. 334 (VPO). nmr. δ, 0 (d, 6, SiC$\underline{H}_3$); 4.1 (septet, 0.9, Si-$\underline{H}$); 7.03 (m, 4.1, φ$\underline{H}$).

To a cold (−5° C.) solution of 1000 ml. of acetone, 40 ml. of water and 0.4 g. of 5% palladium-on-carbon was added slowly 84.0 g of bis(3-dimethylsilylphenyl)carbonate in 200 ml. of acetone over a period of 8 hrs. After the addition was complete, the palladium-on-carbon was removed by filtration. The filtrate was concentrated on a rotary evaporator at room temperature to viscous liquid which solidified upon treatment with pentane. There was obtained 69.0 g (93.2%) of the desired compound. The carbonate was recrystallized from a mixture of chloroform and pentane to yield crystals, m.p. 94°–95° C.

Calcd. for $C_{17}H_{22}Si_2O_5$: C, 56.32; H, 6.12; Si, 15.50; mol. wt. 362.53.

Found: C, 56.08; H, 5.90; Si, 15.59; mol. wt. 362 (MS) nmr: δ, 0 (s, 12, SiC$\underline{H}_3$); 2.5 (b, 1.6, O$\underline{H}$); 7.09–7.45 (m, 8, φ$\underline{H}$).

This monomer is likewise useful in forming high molecular weight polysiloxanylenearylenecarbonates for utilization as high-temperature transparent interlayers.

EXAMPLE 3

Preparation of Bis[4-(1-hydroxy-1,1,3,3-tetramethyldisiloxanyl)-phenyl]carbonate By use of the procedure of Example 2, utilized for the preparation of bis(3-hydroxydimethylsilylphenyl)carbonate, 9.0 g of bis[4-(1,1,3,3-tetramethyldiisiloxanyl)-phenyl]carbonate gave 7.5 g (78%) of the required compound. The carbonate was recrystallized from benzene and hexane solution to yield the pure compound, bis[4-(1-hydroxy-1,1,3,3-tetramethyldisiloxanyl)phenyl]carbonate, m.p. 62°–63° C.

Calcd. for $C_{21}H_{34}Si_4O_7$: C, 49.38; H, 6.71; Si, 21.99; mol. wt. 510.80.

Found: C, 49.44; H, 6.81, Si, 22.11; mol. wt. 502 (VPO). nmr: δ, 0 (s, 12, SiC$\underline{H}_3$); 0.24 (s, 12 SiC$\underline{H}_3$); 1.8 (b, 2, O$\underline{H}$); (m, 10 φ$\underline{H}$).

This new monomer is useful to prepare the corresponding high molecular weight siloxanylenearylenecarbonate polymer, which is useful as a high temperature-resistant transparent interlayer material.

EXAMPLE 4

Preparation of Bis[3-(1-hydroxy-1,1,3,3-tetramethyldisiloxanyl)-phenyl]carbonate To a cold (0° C.) solution of 15.0 g (0.041 mol.) of bis-(3-hydroxydimethylsilylphenyl)carbonate in 75 ml. of toluene and 45 ml. of triethylamine was added 12.0 g (0.13 mol.) of dimethylchlorosilane. After the addition was complete, the mixture was stirred overnight. The amine salt formed was removed by filtration and the filtrate washed three times with aqueous sodium chloride solution. The organic layer was dried over anhydrous magnesium sulfate and concentrated on a rotary evaporator. Bis[3-(1,1,3,3-tetramethyldisiloxanyl)-phenyl]carbonate was obtained as a liquid boiling at 164° C./0.10 mm. in a yield of 17 g. (73%).

Calcd. for $C_{21}H_{34}Si_4O_5$: C, 52.68; H, 7.16, Si, 23.46; mol. wt. 478.80.

Found: C, 52.87; H, 7.27, Si, 23.46; mol. wt. 470 (VPO). nmr: δ, 0–0.2 (d, s, 24, HSiC$\underline{H}_3$, φSiC$\underline{H}_3$) 5.16–4.66 (m, 2, Si$\underline{H}$) 7.9–7.2 (m, 8.2, φ$\underline{H}$).

The bis[3-(1,1,3,3-tetramethyldisiloxanyl)phenyl]carbonate was then converted to the corresponding hydroxy compound by reaction with acetone and water in the presence of palladium-on-carbon catalyst (as per the latter stage of EXAMPLE 2) to the desired bis[3-(1-hydroxy-1,1,3,3-tetramethyldisiloxanyl)phenyl]carbonate, which was isolated as a liquid.

Calcd. for $C_{21}H_{34}Si_4O_7$: C, 49.38; H, 6.74; Si, 21.99; mol. wt. 510.80.

Found: C, 50.33; H, 6.59; Si 21.27; mol. wt. 510 (MS). nmr: δ, 0 (s, 12, SiC$\underline{H}_3$); 0.18 (s, 12, SiC$\underline{H}_3$); 3.6 (b, 3.2, O$\underline{H}$); 7.09–7.39 (m, 8, φ$\underline{H}$).

EXAMPLE 5

To a cold solution of 51.0 g. (0.225 mol.) of 1,4-bis(-hydroxydimethylsilyl)benzene in 300 ml. of dry toluene and 200 ml of distilled pyridine was added 66.0 g. (0.7 mol) of dimethylchlorosilane. After the addition was complete the mixture was stirred overnight. The pyridine salt was removed by filtration and the filtrate was washed three times with sodium chloride solution. The organic layer was dried over anhydrous magnesium sulfate, concentrated on a rotary evaporator and vacuum distilled. The bis[4-(1,1,3,3-tetramethyldisiloxanyl)]benzene was distilled at 62°–63° C./0.02 mm.

The bis[4-(1,1,3,3-tetramethyldisiloxanyl)]benzene was then converted to the corresponding bis[4-(1-hydroxy-1,1,3,3-tetramethyl-disiloxanyl)] benzene by the method described in Example 2. The desired compound melted at 89°–91° C.

This new monomer is useful in forming high molecular weight polysiloxanylenearylene polymers for utilization as high-temperature elastomers.

EXAMPLE 6

Polymerization of Bis(4-hydroxydimethylsilylphenyl)carbonate

Bis(4-hydroxydimethylsilylphenyl)carbonate (3.0 g, 0.0081 mol.) and 30 ml of freshly-distilled pyridine were placed in a 50 ml. round-bottomed flask, equipped with a magnetic stirring bar, a gas inlet tube (which extended just above the reaction mixture), and a gas outlet leading into a sodium hydroxide solution. With the mixture stirred vigorously and cooled by an ice-water bath, phosgene was introduced slowly into the flask. A solid was formed a few minutes and the solution became viscous and caked. Excess phosgene was then removed by sweeping the system with nitrogen. The reaction mixture was diluted with dichloromethane and stirred until the solid formed was partially liquified. The mixture was then poured into methanol and the new polymer purified by redissolving the precipitate in dichloromethane, reprecipitating in methanol four times and drying at 90° C. in vacuum for 24 hours.

The resulting polysiloxanylenearylenecarbonate was obtained in 80 percent yield and has the structure:

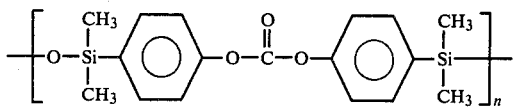

This new polymer had the analyses and characteristics tabulated below in TABLE 1

TABLE 1

| η (dl/g) | Tg (°C.) | NMR | Analyses (Calcd.) & Found | | |
|---|---|---|---|---|---|
| | | | C, % | H, % | Si, % |
| 1.75 | 49 | δ, 0 (s, 12, SiCH₃) 7.03, (m, 8, φH) | 59.05 (59.27) | 5.73 (5.85) | 16.29 (16.30) |

As a general rule, it is recognized that in the art that polysiloxanes having a viscosity of 1.0 dl/g and greater have a molecular weight (number average) of at least about 100,000. This new polymer, having a viscosity of 1.75 dl/g has a molecular weight well in excess of 100,000.

The polymer is useful as a precursor for the development of a heat-stable elastomeric interlayer material upon curing in accordance with known curing techniques. Polymerization of Bis(3-hydroxydimethylsilylphenyl)carbonate The polymerization procedure of EXAMPLE 6 was repeated except for using the new monomer bis(3-hydroxydimethylsilylphenyl)carbonate. The corresponding polysiloxanylenearylenecarbonate was obtained in 47 percent yield and has the structure:

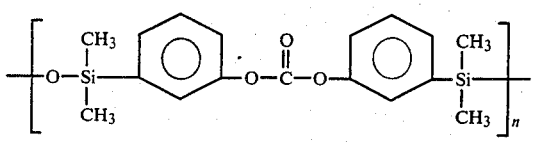

This new polymer had the analyses and characteristics tabulated below in TABLE 2.

TABLE 2

| η (dl/g) | Tg (°C.) | NMR | Analyses (calcd.) & Found | | |
|---|---|---|---|---|---|
| | | | C, % | H, % | Si, % |
| 1.30 | 14 | δ, 0 (S, 12, SiCH₃) 6.90–7.10 (m, 8, φH) | 59.29 (59.27) | 5.87 (5.85) | 16.33 (16.30) |

This new polymer is useful as a high-temperature transparent interlayer when cured.

EXAMPLE 8

Polymerization of Bis(hydroxydimethylsilyl)benzene

The polymerization procedure of EXAMPLE 6 was repeated except using bis(hydroxydimethylsilyl)benzene as monomer. The corresponding polysiloxanylenearylene polymer was obtained in 92 percent yield and has the structure:

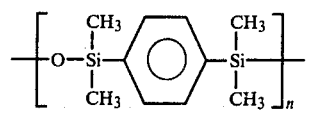

This new polymer had the analyses and characteristics set forth in Table 3.

TABLE 3

| η (dl/g) | Tg (°C.) | NMR | Analyses (Calcd.) & Found | | |
|---|---|---|---|---|---|
| | | | C, % | H, % | Si, % |
| 1.75 | −23 | δ, 0 (s, 12, SiCH₃) 7.20 (s, 4, φH) | 57.31 (57.63) | 7.90 (7.74) | 27.43 (26.96) |

This polysiloxanylenearylene polymer when cured is useful as a base material for the formulation of heat resistant elastomers.

EXAMPLE 9

Polymerization of 4,4'-Bis(hydroxydimethylsilyl)diphenyl ether

The polymerization procedure of EXAMPLE 6 was repeated except for using 4,4'-bis(hydroxydimethylsilyl)diphenyl ether as the monomer. The resulting polysiloxanylenearylene polymer was obtained in 55 percent yield and has the structure:

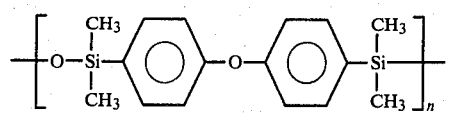

This new polymer was analyzed and has the analyses and characteristics shown in TABLE 4.

TABLE 4

| η (dl/g) | Tg (°C.) | NMR | Analyses (Calcd.) & Found | | |
|---|---|---|---|---|---|
| | | | C, % | H, % | Si, % |
| 1.35 | 17 | δ, 0 (s, 12, (SiCH₃) 6.55–6.75 (d, 4, φOH) 7.05–7.25 (d, 4, SiφH) | 64.05 (63.95) | 7.01 (6.71) | 18.75 (18.70) |

This new polymer is useful for the fabrication of high-temperature elastomers when cured.

EXAMPLE 10

Polymerization of 3,5-Bis[hydroxymethyl(3,3,3-trifluoropropyl)silyl]trifluoromethylbenzene The polymerization procedure of EXAMPLE 6 was repeated except for using 3,5-bis[hydroxymethyl(3,3,3-trifluoropropyl)silyl]trifluoromethylbenzene as monomer. The corresponding trifluoropropylsiloxanylenephenylene polymer was obtained in 43 percent yield and has the structure:

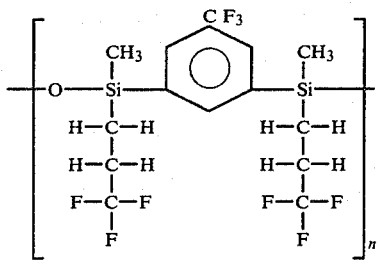

The analytical data and characteristics for this new polymer are set forth in TABLE 5.

TABLE 5

| η (dl/g) | Tg (°C.) | NMR | Analyses (Calcd.) & Found | | |
|---|---|---|---|---|---|
| | | | C, % | H, % | Si, % |
| 1.06 | −13 | δ, 0–0.55 (d, 7, CH₂SiC$\underline{H}$₃) | 42.48 | 4.25 | 35.47 |
| | | 0.9–1.1 (m, 4, C$\underline{H}$₂) | | | |
| | | 7.94 (s, 2, φH) | | | |
| | | 8.12 (s, 1, φH) | (40.90) | (3.89) | (12.15) |

This new polymer is useful as a base material for the formulation of a high-temperature stable aircraft fuel tank sealant.

EXAMPLE 11

Polymerization of a,a'Bis(dimethylhydroxysilyl)-m-xylene

The polymerization procedure of EXAMPLE 6 was repeated except for using a,a'-Bis(dimethylhydroxysilyl)-m-xylene as monomer. The corresponding polysiloxanylenealkarylene polymer was secured in 75 percent yield and has the structure:

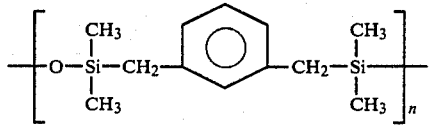

The analytical results and characteristics for this new polymer are given in TABLE 6.

TABLE 6

| η (dl/g) | Tg (°C.) | NMR | Analyses (Calcd.) & Found | | |
|---|---|---|---|---|---|
| | | | C, % | H, % | Si, % |
| 1.02 | −41 | δ, 0 (s, 12, SiC$\underline{H}$₃) | 61.16 | 8.46 | 23.65 |
| | | 2.03 (s, 4, CH) | | | |
| | | 6.4–6.9 (m, 4, φ$\underline{H}$) | (60.96) | (8.53) | (23.76) |

This polymer is useful for the development of heat-resistant elastomers for aerospace applications.

EXAMPLE 12

Polymerization of Bis[3-(1-hydroxy-1,1,3,3-tetramethyldisiloxanyl)-phenyl]carbonate The polymerization procedure of EXAMPLE 6 was followed except for using the present monomer and except for the fact that the reaction mixture was made more concentrated by dissolving bis-silanol (3.0 g) in 10 ml of freshly-distilled pyridine. The reaction mixture, after having been treated with phosgene, was shaken with dichloromethane until a solution was obtained. The solution was concentrated to a small volume on a rotary evaporator before precipitating the polymer from methanol. The resulting polymer was obtained in 54% yield and has the structure:

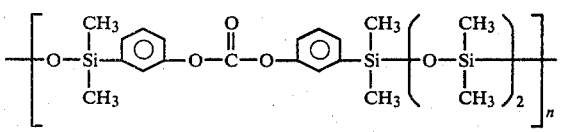

The analytical data and characteristics for this new polysiloxanylene arylene carbonate polymer are set forth in TABLE 7.

TABLE 7

| η (dl/g) | Tg (°C.) | NMR | Analyses (Calcd.) & Found | | |
|---|---|---|---|---|---|
| | | | C, % | H, % | Si, % |
| 1.18 | −35 | δ, 0 (s, 12, SiC$\underline{H}$₃) | 50.90 | 6.74 | 22.83 |
| | | 0.28 (s, 12, SiC$\underline{H}$₃) | | | |
| | | 7.31 (m, 8, φ$\underline{H}$) | (51.18) | (6.54) | (22.80) |

This new polymer is useful when cured for preparation of heat-resistant transparent interlayers for aircraft windshield and canopy assemblies.

EXAMPLE 13

Nine weight parts of the monomer of Example 12 was copolymerized with one weight part of bis[3-(1-hydroxy-1-vinyl-1,3,3-trimethyldisiloxanyl)phenyl]carbonate to yield the desired copolymer having a viscosity of 1.2 dl/g. and a transition temperature, Tg, of −37° C. This copolymer is useful as a readily curable transparent interlayer material, curable in accordance with known procedures, e.g., peroxide curing systems, and has the structure:

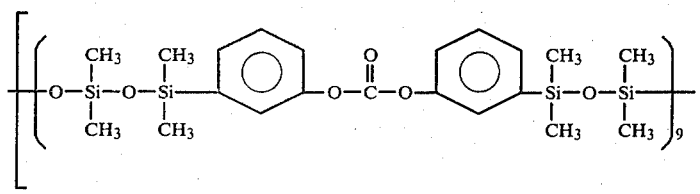

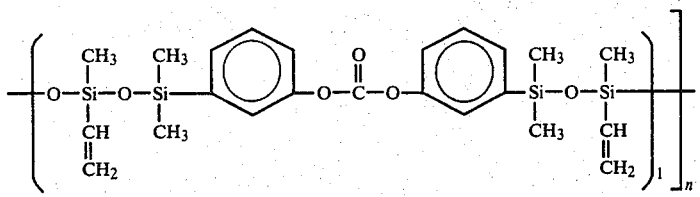

EXAMPLE 14

Polymerization of Bis[4-(1-hydroxy-1,1,3,3-tetramethyldisiloxanyl)-phenyl]carbonate That polymerization procedure of EXAMPLE 12 was followed except that the subject monomer was used rather than the analogous meta-substituted monomer of EXAMPLE 12. The resulting homopolymer was obtained in 77 percent yield and has the structure:

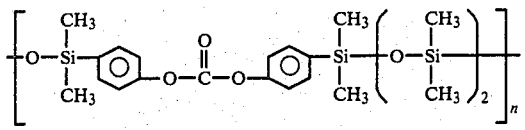

The analytical data and characteristics for this new polysiloxanylenearylenecarbonate polymer are shown in TABLE 8.

TABLE 8

| η (dl/g) | Tg (°C.) | NMR | Analyses (Calcd.) & Found | | |
|---|---|---|---|---|---|
| | | | C, % | H, % | Si, % |
| 1.40 | −24 | δ, 0–0.25 (s, s, 25, SiCH₃) | 51.17 | 6.76 | 22.56 |
| | | 7.32 (m, 8, φH) | (51.18) | (6.54) | (22.80) |

This new polymer is useful as the curable base material for high temperature transparent interlayers.

EXAMPLE 15

Polymerization of 1,4-Bis(1-hydroxy-1,1,3,3-tetramethyldisiloxanyl)benzene

The polymerization procedure of EXAMPLE 12 was repeated except that the subject monomer was employed. The resulting siloxanylenearylene polymer was obtained in 84 percent yield and has the structure:

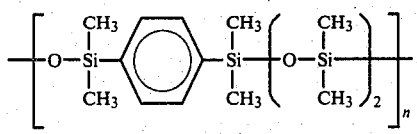

The analytical data and characteristics for this new polymer are set forth in TABLE 9.

TABLE 9

| η (dl/g) | Tg (°C.) | NMR | Analyses (Calcd.) & Found | | |
|---|---|---|---|---|---|
| | | | C, % | H, % | Si, % |
| 1.60 | −77 | δ, 0 (s, 12, SiCH₃) | 47.55 | 8.41 | 31.47 |
| | | 0.28 (s, 12, SiCH₃) | | | |
| | | 7.48 (m, 4, φH) | (47.14) | (7.91) | (31.50) |

This new polymer is useful as a readily curable thermally stable elastomer for aerospace applications such as an interlayer, tank sealant, etc.

We claim:

1. A process for making arylene siloxanylene polymers which comprises contacting a monomer of the formula

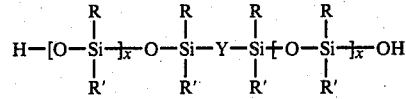

wherein Y is an arylene or substituted arylene moiety; R and R' are lower alkyl, substituted lower alkyl or phenyl, and x is an integer having a value of 0 or 1; with phosgene in the presence of an aromatic heterocyclic amine inert to reaction with phosgene.

2. The process of claim 1 wherein said amine is pyridine.

3. The process of claim 1 wherein Y is selected from the group consisting of

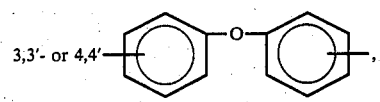
3,3'- or 4,4'-

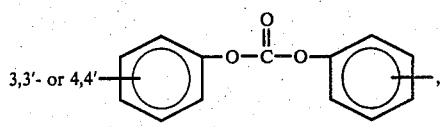
3,3'- or 4,4'-

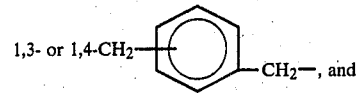
1,3- or 1,4-CH₂—       —CH₂—, and

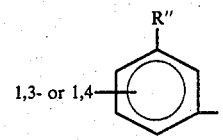
1,3- or 1,4- wherein R" is selected from the group consisting of —H, methyl and trifluoromethyl.

4. The process of claim 1 which further comprises the step of combining a co-monomer with said monomer, and thereafter contacting said monomer and said co-monomer with said phosgene in the presence of said aromatic heterocyclic amine, wherein said co-monomer is different from said monomer, said co-monomer having at least one R or R' which is a vinyl group.

* * * * *

UNITED STATES PATENT OFFICE
CERTIFICATE OF CORRECTION

PATENT NO. : 4,366,323
DATED : December 28, 1982
INVENTOR(S) : Harold Rosenberg et al It is certified that error appears in the above-identified patent and that said Letters Patent are hereby corrected as shown below:

Column 1, line 60, "sfaety" should read "safety". Column 6, line 49, "170°1/4°C/0.10mm" should read "170-174°C/0.10 mm". Columns 7 and 8, Equation (5), the arrowhead should point to the right.

Signed and Sealed this

Twelfth Day of April 1983

[SEAL]

Attest:

GERALD J. MOSSINGHOFF

Attesting Officer    Commissioner of Patents and Trademarks